United States Patent
Warner et al.

(10) Patent No.: US 7,876,875 B2
(45) Date of Patent: Jan. 25, 2011

(54) COMPUTED TOMOGRAPHY SYSTEMS AND RELATED METHODS INVOLVING MULTI-TARGET INSPECTION

(75) Inventors: Rodney H. Warner, Austin, TX (US); Royce McKim, Austin, TX (US)

(73) Assignee: United Technologies Corp., Hartford, CT (US)

( * ) Notice: Subject to any disclaimer, the term of this patent is extended or adjusted under 35 U.S.C. 154(b) by 70 days.

(21) Appl. No.: 12/099,899

(22) Filed: Apr. 9, 2008

(65) Prior Publication Data

US 2009/0257552 A1    Oct. 15, 2009

(51) Int. Cl.
- *A61B 6/03* (2006.01)
- *H05G 1/60* (2006.01)
- *H05G 1/64* (2006.01)
- *G01N 23/083* (2006.01)

(52) U.S. Cl. .............................. 378/20; 378/10; 378/57; 378/58; 378/208

(58) Field of Classification Search .................. 378/10, 378/20, 57, 58, 68, 71, 73, 79, 81, 195, 196, 378/208, 209
See application file for complete search history.

(56) References Cited

U.S. PATENT DOCUMENTS

| | | | |
|---|---|---|---|
| 2,741,710 A | 4/1956 | Bartow et al. | |
| 4,054,800 A | 10/1977 | Leask | |
| 4,211,927 A | 7/1980 | Hellstrom et al. | |
| 4,242,587 A | 12/1980 | Lescrenier | |
| 4,453,226 A | 6/1984 | Hobbs et al. | |
| 4,521,372 A | 6/1985 | Price et al. | |
| 4,558,458 A | 12/1985 | Katsumata et al. | |
| 4,590,658 A | 5/1986 | Funyu et al. | |
| 4,599,740 A | 7/1986 | Cable | |
| 4,636,475 A | 1/1987 | Price et al. | |
| 4,691,332 A | 9/1987 | Burstein et al. | |
| 4,821,511 A | 4/1989 | Felix et al. | |
| 4,825,454 A | 4/1989 | Annis et al. | |
| 4,872,191 A * | 10/1989 | Bernardi | 378/150 |
| 4,969,110 A * | 11/1990 | Little et al. | 382/131 |
| 4,989,225 A | 1/1991 | Gupta et al. | |
| 5,119,408 A * | 6/1992 | Little et al. | 378/4 |
| 5,131,021 A | 7/1992 | Gard et al. | |
| 5,140,661 A | 8/1992 | Kerek | |

(Continued)

FOREIGN PATENT DOCUMENTS

JP    60256034    12/1985

(Continued)

OTHER PUBLICATIONS

"Scientific Papers", Molecular Imaging and Biology, vol. 8, No. 2, Mar. 1, 2006, pp. 49-123.

(Continued)

*Primary Examiner*—Allen C. Ho

(57) ABSTRACT

Computed tomography (CT) systems and related methods involving multi-target inspection are provided are provided. In this regard, a representative method includes: simultaneously directing X-rays toward multiple targets from an X-ray source; during the directing of the X-rays, independently reorienting the targets with respect to the X-ray source; and obtaining information corresponding to attenuation of the X-rays attributable to the multiple targets for producing computed tomography images of the targets.

10 Claims, 4 Drawing Sheets

U.S. PATENT DOCUMENTS

| | | | |
|---|---|---|---|
| 5,222,114 A | 6/1993 | Kamata et al. | |
| 5,430,298 A | 7/1995 | Possin et al. | |
| 5,442,179 A | 8/1995 | Ohishi | |
| 5,550,378 A | 8/1996 | Skillicorn et al. | |
| 5,555,283 A | 9/1996 | Shiu et al. | |
| 5,652,429 A | 7/1997 | Genna | |
| 5,799,057 A | 8/1998 | Hoffman et al. | |
| 5,889,834 A | 3/1999 | Vilsmeier et al. | |
| 5,930,326 A | 7/1999 | Rothschild et al. | |
| 5,982,846 A | 11/1999 | Toth et al. | |
| 5,991,357 A | 11/1999 | Marcovici et al. | |
| 6,041,132 A * | 3/2000 | Isaacs et al. | 382/100 |
| 6,104,776 A * | 8/2000 | Oikawa | 378/22 |
| 6,167,110 A | 12/2000 | Possin et al. | |
| 6,188,748 B1 | 2/2001 | Pastyr et al. | |
| 6,229,872 B1 | 5/2001 | Amos | |
| 6,438,210 B1 | 8/2002 | Castleberry | |
| 6,457,862 B1 * | 10/2002 | Sumii et al. | 378/208 |
| 6,487,267 B1 | 11/2002 | Wolter | |
| 6,639,964 B2 | 10/2003 | Schneider et al. | |
| 6,671,541 B2 | 12/2003 | Bishop et al. | |
| 6,703,622 B2 | 3/2004 | Joubert | |
| 6,868,138 B2 | 3/2005 | Clinthorne et al. | |
| 6,879,715 B2 | 4/2005 | Edic et al. | |
| 6,925,140 B2 | 8/2005 | Bruder | |
| 6,934,642 B2 | 8/2005 | Berry et al. | |
| 6,979,826 B2 | 12/2005 | Ikhlef | |
| 7,095,028 B2 | 8/2006 | Mollov et al. | |
| 7,099,435 B2 | 8/2006 | Heumann et al. | |
| 7,115,876 B2 | 10/2006 | Ren et al. | |
| 7,120,282 B2 | 10/2006 | Langan | |
| 7,133,491 B2 | 11/2006 | Bernardi et al. | |
| 7,177,388 B2 * | 2/2007 | Takagi et al. | 378/20 |
| 7,185,662 B2 | 3/2007 | Succop | |
| 7,187,800 B2 | 3/2007 | Hibbard | |
| 7,188,998 B2 | 3/2007 | Gregerson et al. | |
| 7,204,019 B2 | 4/2007 | Ducotey et al. | |
| 7,216,694 B2 | 5/2007 | Otero et al. | |
| 7,221,737 B2 | 5/2007 | Hoheisel et al. | |
| 7,236,564 B2 | 6/2007 | Hopkins et al. | |
| 7,254,209 B2 | 8/2007 | Zhao et al. | |
| 7,254,211 B2 * | 8/2007 | Hunt et al. | 378/20 |
| 7,272,207 B1 | 9/2007 | Aufrichtig et al. | |
| 7,283,605 B2 | 10/2007 | Sainath et al. | |
| 7,283,608 B2 | 10/2007 | Hoffman | |
| 7,283,616 B2 | 10/2007 | Freund et al. | |
| 7,286,630 B2 * | 10/2007 | Holt | 378/8 |
| 7,286,636 B2 | 10/2007 | Unger et al. | |
| 7,341,376 B2 | 3/2008 | Birdwell et al. | |
| 7,356,115 B2 * | 4/2008 | Ford et al. | 378/57 |
| 7,492,862 B2 * | 2/2009 | Bendahan | 378/57 |
| 2001/0040219 A1 | 11/2001 | Cherry et al. | |
| 2002/0097836 A1 | 7/2002 | Grodzins | |
| 2006/0133565 A1 | 6/2006 | Takagi et al. | |
| 2007/0064878 A1 | 3/2007 | Heismann | |
| 2008/0075227 A1 | 3/2008 | Christoph et al. | |
| 2008/0298546 A1 | 12/2008 | Bueno et al. | |

FOREIGN PATENT DOCUMENTS

| | | |
|---|---|---|
| JP | 05309088 | 11/1993 |
| JP | 06237927 | 8/1994 |
| JP | 08187239 | 7/1996 |

OTHER PUBLICATIONS

Sun et al., "X-Ray Microcomputed Tomography for Measuring Polymerization Shrinkage of Polymeric Dental Composites", Dental Materials, vol. 24, No. 2, Dec. 26, 2007, pp. 228-234.

Johnson et al., "Virtual Histology of Transgenic Mouse Embryos for High-Throughput Penotyping", PLOS Genetices, vol. 2, No. 4, Apr. 2006, pp. 471-477.

Dufresne, T. "Segmentation Techniques for Analysis of Bone by Three-Dimensional Computed Tomographic Imaging", Technology and Health Care, vol. 6, No. 5/06, Dec. 1, 1998, pp. 351-359.

Kai Wang et al. "Surface Detection With Subvoxel Accuracy Using Facet Model and IDDG Operator", Computer-Aided Industrial Design and Conceptual Design, 2006, Nov. 17, 2006, pp. 1-5.

Andrew Burghardt et al. "A Local Adaptive Threshold Strategy for High Resolution Peripheral Quantitative Computer Tomography of Trabecular Cone", Annals of Biomedical Engineering, vol. 35, No. 10, Jun. 30, 2007, pp. 1678-1686.

Oh W et al. "Image Thresholding by Indicator Kriging", IEE Transactions on Pattern Analysis and Machine Intelligence, vol. 21, No. 7, Jul. 1, 1999, pp. 590-602.

* cited by examiner

COMPUTED TOMOGRAPHY SYSTEMS AND RELATED METHODS INVOLVING MULTI-TARGET INSPECTION

BACKGROUND

1. Technical Field

The disclosure generally relates to non-destructive inspection of components.

2. Description of the Related Art

Computed tomography (CT) involves the use of X-rays that are passed through a target. Based on the amount of X-ray energy detected at a detector located downstream of the target, information about the target can be calculated. By way of example, representations of target shape and density in three dimensions can be determined.

SUMMARY

Computed tomography systems and related methods involving multi-target inspection are provided. In this regard, an exemplary embodiment of a computed tomography system for multi-target inspection comprises: a multi-target positioning unit having multiple target supports, each of the target supports being located along a corresponding line of sight of an X-ray source of the system, the target supports being operative to orient multiple targets simultaneously such that each of the multiple targets is positionable at multiple orientations.

An exemplary embodiment of a method for performing computed tomography on multiple targets comprises: simultaneously directing X-rays toward multiple targets from an X-ray source; during the directing of the X-rays, independently reorienting the targets with respect to the X-ray source; and obtaining information corresponding to attenuation of the X-rays attributable to the multiple targets for producing computed tomography images of the targets.

Other systems, methods, features and/or advantages of this disclosure will be or may become apparent to one with skill in the art upon examination of the following drawings and detailed description. It is intended that all such additional systems, methods, features and/or advantages be included within this description and be within the scope of the present disclosure.

BRIEF DESCRIPTION OF THE DRAWINGS

Many aspects of the disclosure can be better understood with reference to the following drawings. The components in the drawings are not necessarily to scale. Moreover, in the drawings, like reference numerals designate corresponding parts throughout the several views.

DETAILED DESCRIPTION

Computed tomography (CT) systems and related methods involving multi-target inspection are provided, several exemplary embodiments of which will be described in detail. In this regard, CT involves passing X-rays through a target and measuring attenuation of the X-rays using a set of detectors. In some embodiments, a multi-target positioning unit is used to position two or more targets for simultaneous inspection. By using such a multi-target positioning device, inspection time can be reduced.

Figure 1:
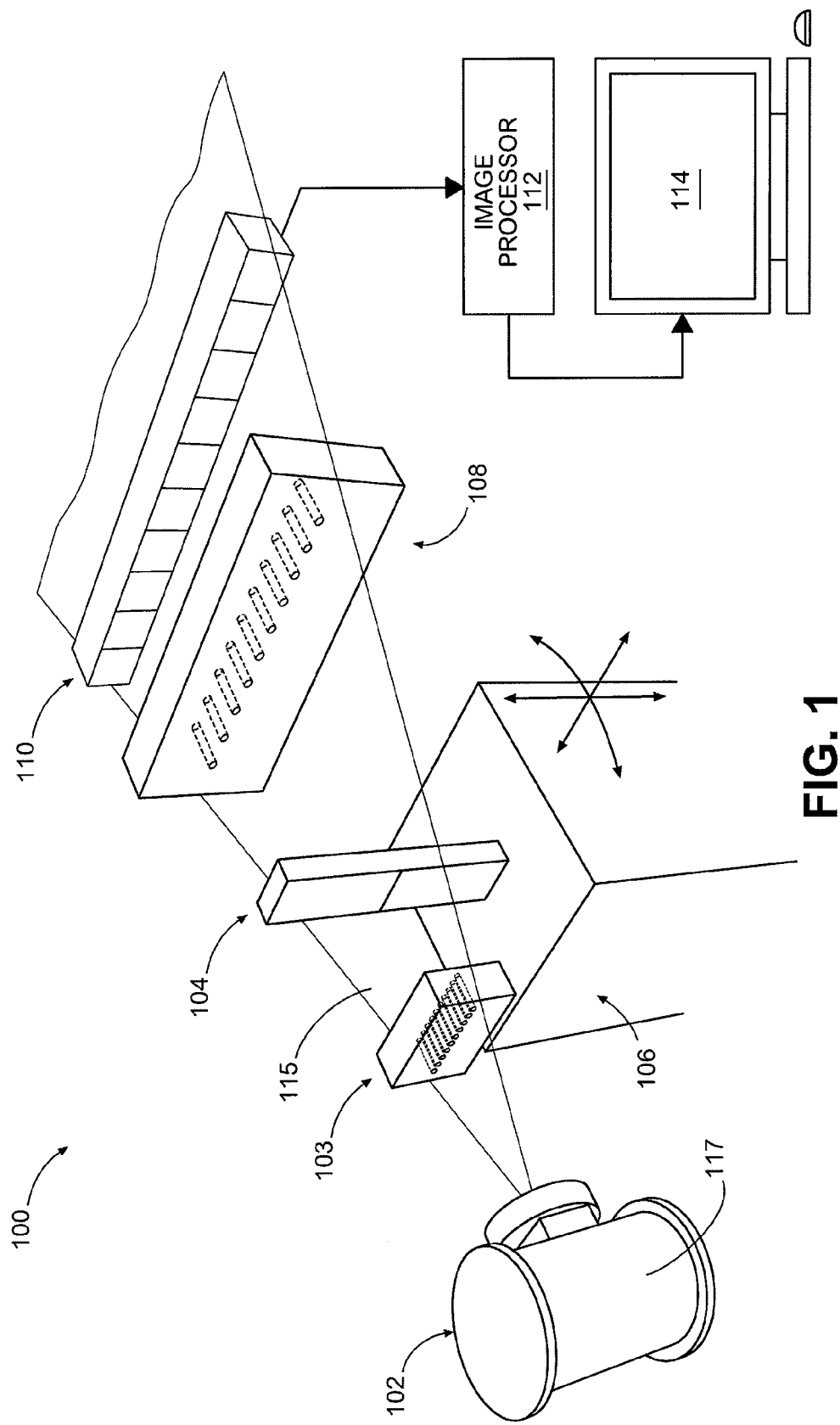
FIG. 1 is a schematic diagram depicting an exemplary embodiment of a system involving multi-target inspection.

In this regard, FIG. 1 is a schematic diagram depicting an exemplary embodiment of a system involving multi-target inspection. As shown in FIG. 1, system 100 includes an X-ray source 102, an optional pre-target collimator 103, a target 104 positioned on a multi-target positioning unit 106, an optional post-target collimator 108, an array of detectors 110, an image processor 112, and a display/analysis system 114. In operation, X-ray source 102 (e.g., a spot source) is operative to emit X-rays. In this embodiment, the X-rays are emitted as a fan-shaped beam 115. Notably, source 102 incorporates an integrated source collimator (not shown in FIG. 1) within a housing 117 in order to limit X-rays generated at the source to the fan-shaped beam.

Multi-target positioning unit 106 is a representative apparatus used for positioning one or more targets, in this case, target 104. In operation, multi-target positioning unit 106 exposes various portions of each of the targets to the X-rays emitted by source 102. In this embodiment, the multi-target positioning unit can be used to rotate target 104 both clockwise and counterclockwise, as well as to raise and lower the target. Altering of a vertical position of the target in this embodiment is accomplished to expose different heights (e.g., horizontal planes) of the target to the fan-shaped beam. Notably, the elevation of the beam is fixed in this embodiment.

Each of the collimator 103, 108 includes an array of channels through which X-rays can pass. Material defining the channels is relatively X-ray absorbing, thereby substantially preventing the passage of X-rays through other than the channels. In the embodiment of FIG. 1, tungsten is used although, in other embodiments, various other materials can be used such as brass or lead, for example.

Detector array 110 is positioned downstream of post-target collimator 108. The detector array is operative to output signals corresponding to an amount of X-rays detected. In this embodiment, the array is a linear array, although various other configurations can be used in other embodiments.

Image processor 112 receives information corresponding to the amount of X-rays detected by the detector array and uses the information to compute image data corresponding to the target. The image data is provided to display/analysis system 114 to enable user interaction with the information acquired by the detector array.

Figure 2:
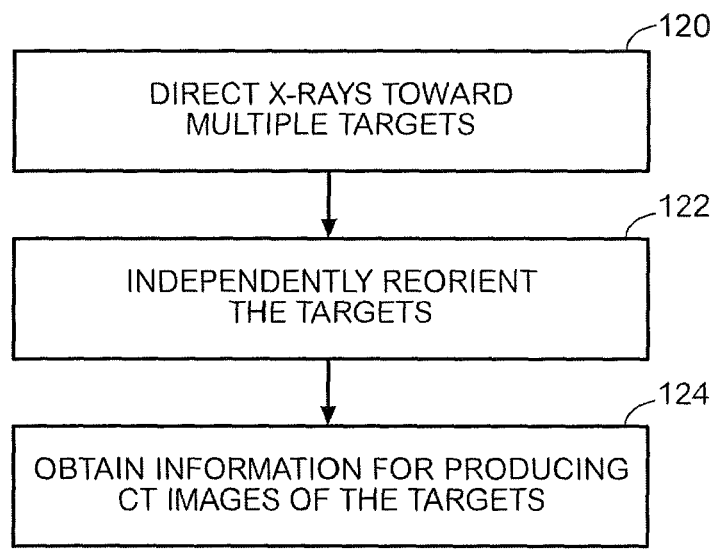
FIG. 2 is a flowchart depicting an exemplary embodiment of a method involving multi-target inspection.

FIG. 2 is a schematic diagram an exemplary embodiment of a method involving multi-target inspection such that that which maybe performed by the system of FIG. 1. As shown in FIG. 2, the method (or functionality) may be construed as beginning at block 120, in which X-rays are simultaneously directed toward multiple targets from an X-ray source. In block 122, during the directing of the X-rays, the targets are independently reoriented with respect to the X-ray source. In some embodiments, each of the targets is independently supported by a corresponding movable support. As such, the targets can be moved separately in some embodiments, whereas, in others, the targets can be reoriented in synchronization with each other. As depicted in block 124, information corresponding to attenuation of the X-rays attributable to the multiple targets is obtained for producing computed tomography images of the targets. Notably, obtaining of the information can be performed simultaneously with the reorienting of the targets.

In some embodiments, the X-rays can be collimated prior to reaching the targets. Notably, this can be in addition to collimation that occurs internal to a housing that is used to encase an X-ray emitter. Additionally or alternatively, the X-rays can be collimated downstream of the targets and prior to reaching an array of detectors.

Computed tomography images of the targets can be used to perform non-destructive inspection in order to determine one or more of various characteristics. By way of example, the characteristics can include, but are not limited to, interior shape and density of each of the targets. In some embodiments, the targets can be a formed of metal. Additionally or alternatively, the targets can be gas turbine engine components, such as turbine blades.

Figure 3:
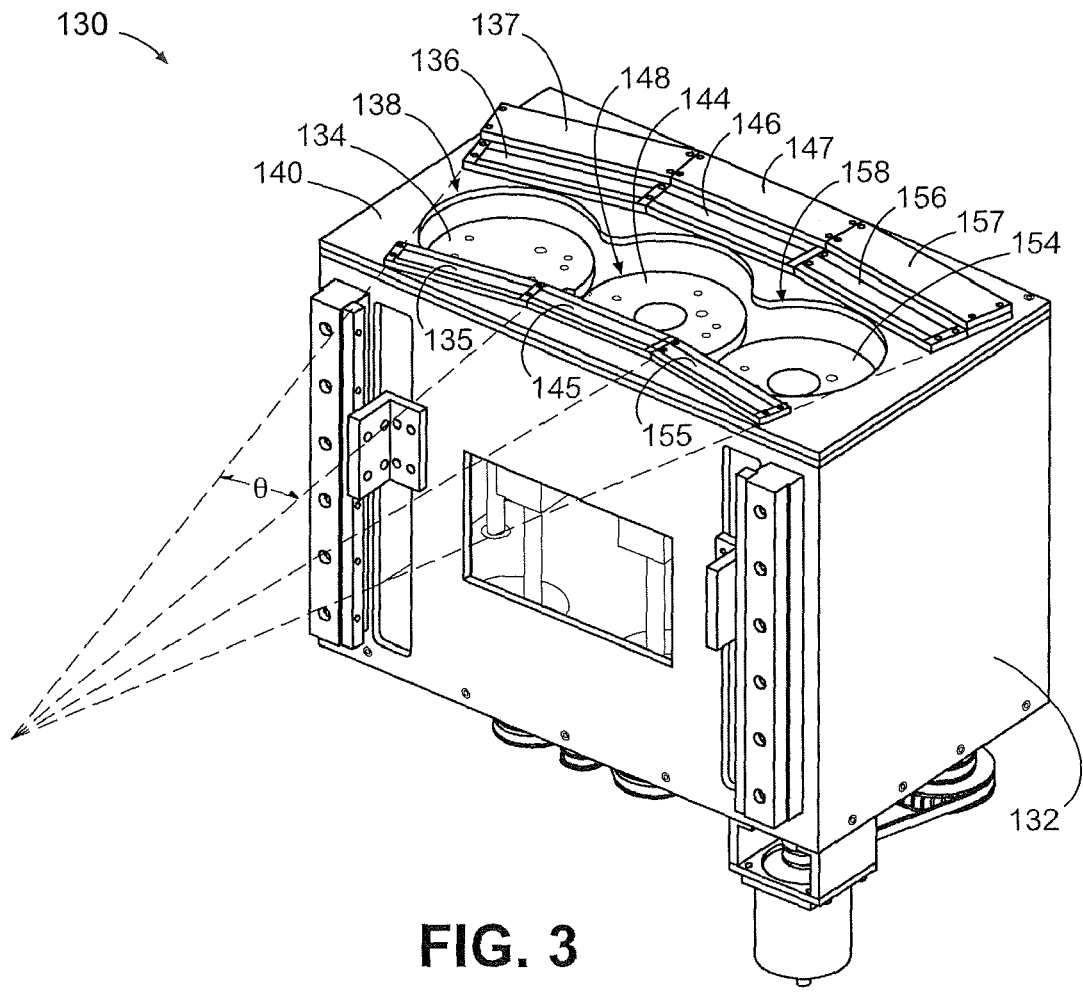
FIG. 3 is a schematic diagram depicting another exemplary embodiment of a system involving multi-target inspection.

FIG. 3 is a schematic diagram depicting another exemplary embodiment of a system involving multi-target inspection. In particular, FIG. 3 schematically depicts another embodiment of a multi-target positioning unit. As shown in FIG. 3, unit 130 includes a housing 132 that supports three targets supports (134, 144 and 154). A working surface 140 of the housing supports three pre-target collimators (135, 145 and 155), three post-target collimators (136, 146 and 156) and three detector arrays (137, 147 and 157). Pre-target collimator 135, target support 134, post-target collimator 136 and detector array 137 define a first set of inspection components aligned for inspecting a target (not shown) located on target support 134; pre-target collimator 145, target support 144, post-target collimator 146 and detector array 147 define a second set aligned for inspecting a target (not shown) located on target support 144; and pre-target collimator 155, target support 154, post-target collimator 156 and detector array 157 define a third set aligned for inspecting a target (not shown) located on target support 154.

Each of the sets of inspection components is oriented within a corresponding arc of an X-ray source. By way of example, if the X-ray source emits a 30 degree fan-shaped beam of X-rays and a multi-target positioning unit includes three set of inspection components, each of the sets of inspection components can be placed along a corresponding 10 degree arc (i.e., within 10 degrees of azimuth (θ) from the X-ray source). In other embodiments, various other numbers of sets of inspection components, other extents of fan-shaped beams and component positions can be used.

Working surface 140 also includes cutouts (138, 148, and 158) that are configured to receive corresponding target supports so that the target supports can be raised and lowered through the cutouts. This permits different horizontal planes of each of the targets to be exposed to the fan-shaped beam as the target supports are reoriented relative to the sets of inspection components.

Figure 4:
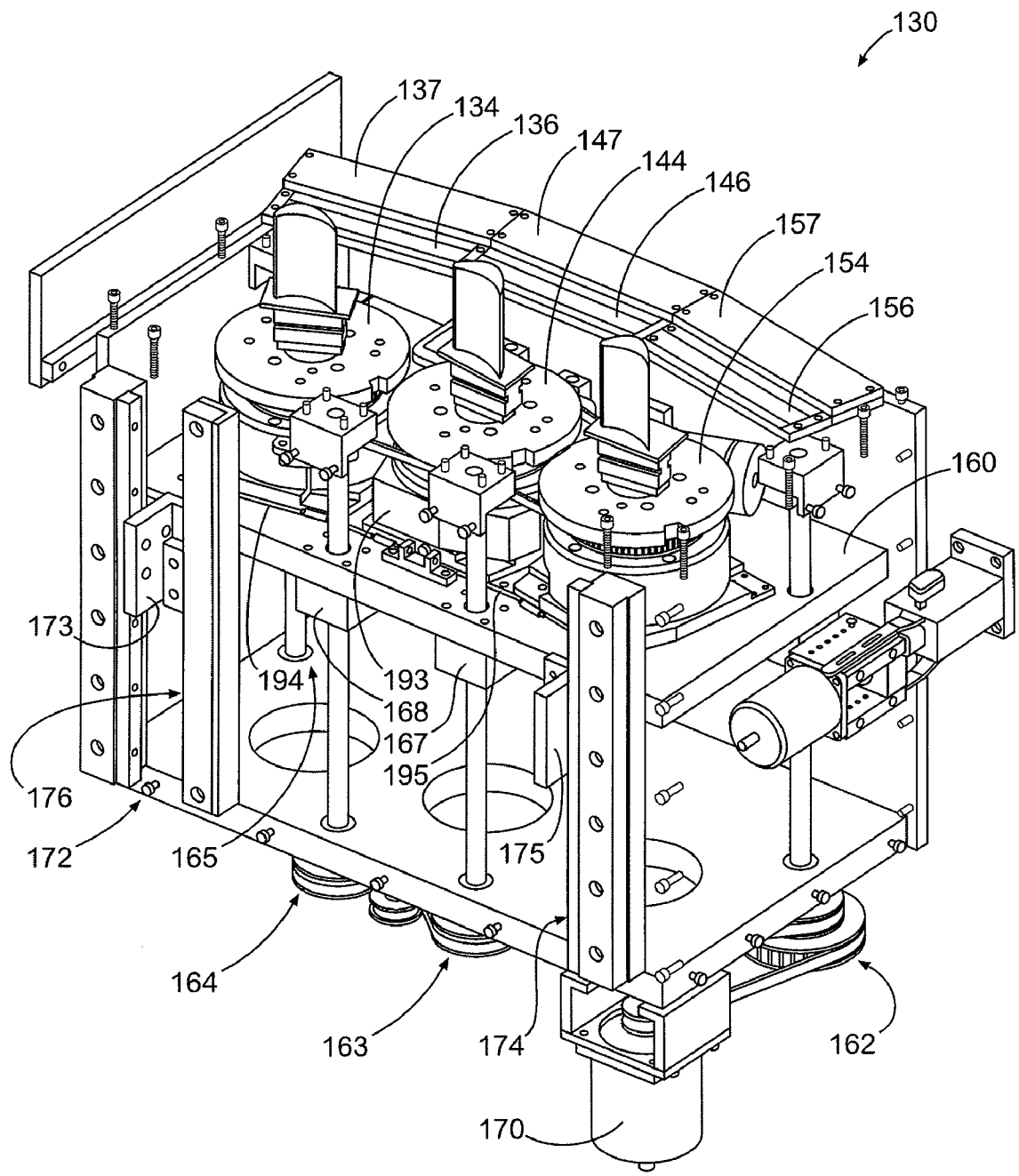
FIG. 4 is a schematic diagram showing detail of a portion of the embodiment of FIG. 3.
Figure 5:
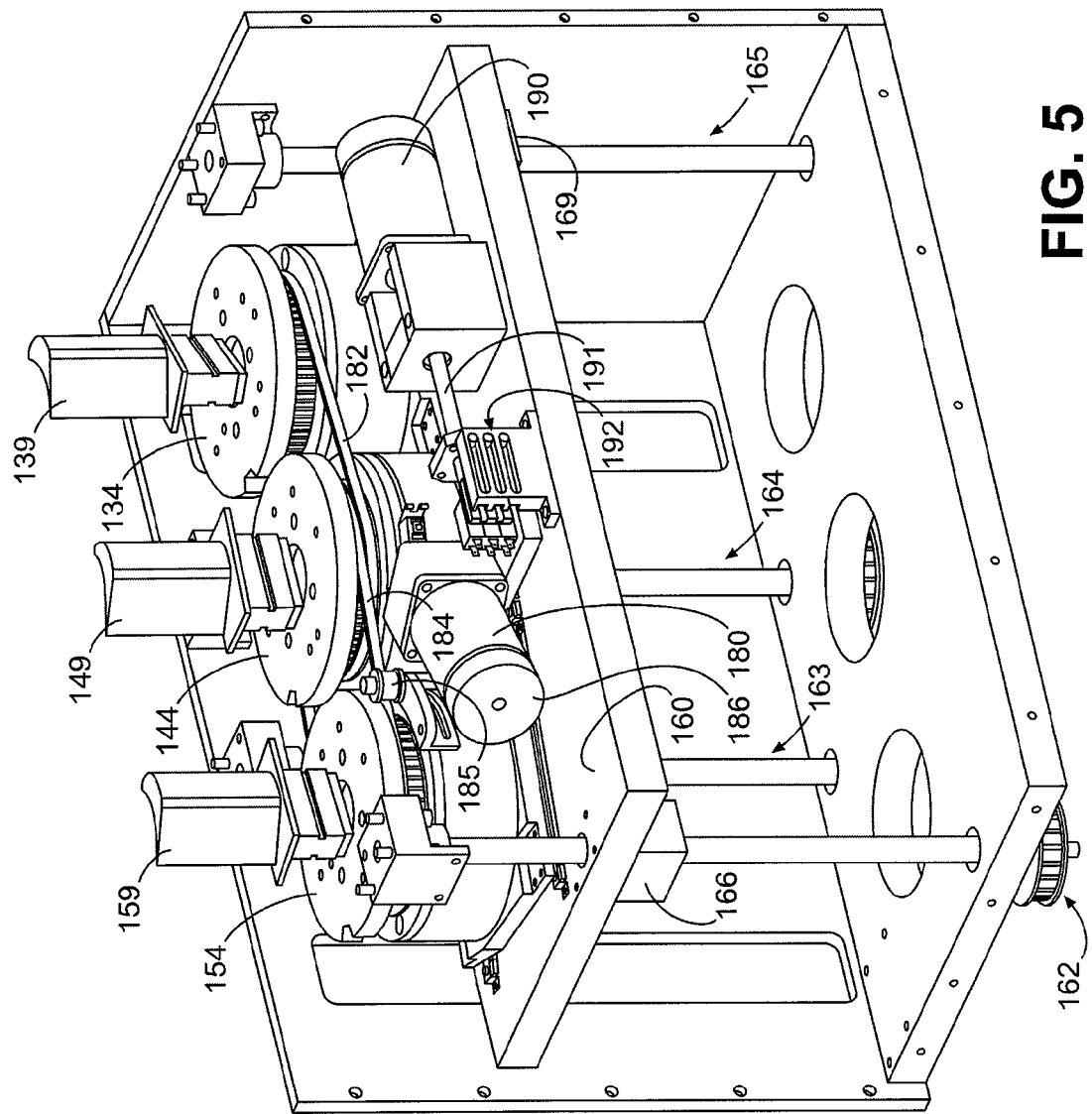
FIG. 5 is a schematic diagram showing detail of another portion of the embodiment of FIG. 3.

As shown in greater detail in FIGS. 4 and 5, which shows unit 130 with various portions of the housing removed for ease of illustration, the target supports (134, 144 and 154) are mounted to a carrier 160. Carrier 160 is configured as a platform in this embodiment that is moved to establish vertical positions of the target supports. In particular, unit 130 includes jacks that engage and move the carrier. Specifically, each of the jacks includes a threaded shaft and a ball nut, which rides along the threaded shaft as the shaft rotates. In this embodiment, four jacks (162, 163, 164 and 165) include corresponding ball nuts (166, 167, 168 and 169) that are mounted to the underside of carrier 160. A drive motor 170 is mechanically coupled to the jacks for rotating the shafts in unison. As such, the carrier and the target supports can be raised or lowered depending upon a direction of rotation of drive motor 170. Notably, in this embodiment, drive belts are used to mechanically couple the jacks to the drive motor.

Guide rails 172, 174 are used to prevent misalignment of the carrier during transit. The guide rails engage corresponding guides 173, 175 that extend from the carrier. In this embodiment, an encoder 176 is used to provide information regarding a current vertical position of the carrier and, thus, of targets supported by the target supports.

As shown more clearly in FIG. 5, a drive motor 180 is used to rotate the target supports (134, 144 and 154) upon which representative targets 139, 149 and 159 are positioned. Drive motor 180 is configured as a worm gear in this embodiment that directly drives target support 144. Following mechanisms (e.g., belts) 182, 184 engage target support 144 and are used to drive target supports 134 and 154 respectively. In this embodiment, each of the belts 182, 184 is tensioned by a corresponding tensioner. For instance, belt 184 is tensioned by tensioner 185. An encoder 186 is used to provide information corresponding to rotational positions of the target supports.

As shown in FIGS. 4 and 5, a drive motor 190 is used to translate the target supports laterally. Specifically, drive motor 190 drives target support 144 along rails 193 using a ball screw 191 and a jack nut 192. Target supports 134 and 154 are mechanically linked to target support 144 so that drive motor 190 translates the target supports in unison. In this regard, target support 134 rides along rails 194 and target support 154 rides along rails 195. Notably, rails 194 and 195 are angularly displaced with respect to rail 193, with displacement of each in this embodiment being approximately 10 degrees.

In operation, drive motor 190 is used to alter the lateral position of the targets within the fan-shaped beam of X-rays. After rotating the target and acquiring the desired information, the target supports are translated in order to align different portions of the targets with the X-ray detectors. The targets are rotated again and more information is acquired. This process may repeat as necessary to ensure adequate acquisition of information.

It should be noted that a computing device can be used to implement various functionality, such as that attributable to the image processor 112 and/or display/analysis system 114 depicted in FIG. 1. In terms of hardware architecture, such a computing device can include a processor, memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and receivers to enable communications. Further, the local interface may include address, control, and/or data connections to enable appropriate communications among the aforementioned components.

The processor may be a hardware device for executing software, particularly software stored in memory. The processor can be a custom made or commercially available processor, a central processing unit (CPU), an auxiliary processor among several processors associated with the computing device, a semiconductor based microprocessor (in the form of a microchip or chip set) or generally any device for executing software instructions.

The memory can include any one or combination of volatile memory elements (e.g., random access memory (RAM, such as DRAM, SRAM, SDRAM, VRAM, etc.)) and/or non-volatile memory elements (e.g., ROM, hard drive, tape, CD- ROM, etc.). Moreover, the memory may incorporate electronic, magnetic, optical, and/or other types of storage media. Note that the memory can also have a distributed architecture, where various components are situated remotely from one another, but can be accessed by the processor.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The Input/Output devices that may be coupled to system I/O Interface(s) may include input devices, for example but not limited to, a keyboard, mouse, scanner, microphone, camera, proximity device, etc. Further, the Input/Output devices may also include output devices, for example but not limited to, a printer, display, etc. Finally, the Input/Output devices may further include devices that communicate both as inputs and outputs, for instance but not limited to, a modulator/demodulator (modem; for accessing another device, system, or network), a radio frequency (RF) or other transceiver, a telephonic interface, a bridge, a router, etc.

When the computing device is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed.

It should be emphasized that the above-described embodiments are merely possible examples of implementations set forth for a clear understanding of the principles of this disclosure. Many variations and modifications may be made to the above-described embodiments without departing substantially from the spirit and principles of the disclosure. All such modifications and variations are intended to be included herein within the scope of this disclosure and protected by the accompanying claims.

The invention claimed is:

1. A computed tomography system for multi-target inspection comprising:
   an X-ray source;
   a multi-target positioning unit having multiple target supports, each of the multiple target supports being located along a corresponding line of sight of the X-ray source of the system, the multiple target supports being operative to orient multiple targets simultaneously such that each of the multiple targets is positionable at multiple orientations;
   wherein the multi-target positioning unit has a carrier operative to support the multiple target supports and to move the multiple target supports vertically relative to the X-ray source; and
   wherein the multiple target supports are operable to move laterally relative to the carrier;
   wherein each of the multiple target supports is rotatable to rotate a target; and
   wherein the multi-target positioning unit has a drive motor and a following mechanism, the drive motor being operative to drive a first of the multiple target supports, the following mechanism being driven by the first of the multiple target supports and being operative to drive a second of the multiple target supports.

2. The system of claim 1, wherein the following mechanism is a belt.

3. The system of claim 2, wherein the multiple target supports are operative to alter vertical positions of the multiple targets in synchronization with each other.

4. A computed tomography system for multi-target inspection comprising:
   an X-ray source;
   a multi-target positioning unit having multiple target supports, each of the multiple target supports being located along a corresponding line of sight of the X-ray source of the system, the multiple target supports being operative to orient multiple targets simultaneously such that each of the multiple targets is positionable at multiple orientations;
   wherein the multi-target positioning unit has a carrier operative to support the multiple target supports and to move the multiple target supports vertically relative to the X-ray source; and
   wherein the multiple target supports are operable to move laterally relative to the carrier; and
   wherein:
      the multi-target positioning unit includes multiple jacks operative to raise and lower the carrier; and
      at least a first one of the multiple jacks has a threaded shaft and a ball nut, the ball nut being coupled to the carrier and being operative to ride along the shaft in a direction corresponding to a direction of rotation of the shaft.

5. The system of claim 4, wherein:
   the multi-target positioning unit has a drive motor; and
   the multiple jacks are driven by the drive motor.

6. A computed tomography system for multi-target inspection comprising:
   an X-ray source;
   a multi-target positioning unit having multiple target supports, each of the multiple target supports being located along a corresponding line of sight of the X-ray source of the system, the multiple target supports being operative to orient multiple targets simultaneously such that each of the multiple targets is positionable at multiple orientations;
   wherein the multi-target positioning unit has a carrier operative to support the multiple target supports and to move the multiple target supports vertically relative to the X-ray source; and
   wherein the multiple target supports are operable to move laterally relative to the carrier; and
   wherein each of the multiple target supports is operable to move laterally along a set of rails, and where each set of rails is angularly displaced with respect to adjacent sets of rails.

7. A multi-target positioning system for an X-ray computed tomography system, comprising:
   a housing having a working surface;
   a plurality of X-ray detector arrays mounted to the working surface of the housing, each of the plurality of X-ray detector arrays being angularly offset from an adjacent one of the plurality of X-ray detector arrays; and
   a plurality of target supports disposed with the housing, and operable to at least one of move vertically, move laterally and rotate relative to the plurality of X-ray detector arrays, each target support independently aligned with a respective one of the plurality of X-ray detector arrays.

8. The system of claim 7, wherein the plurality of target supports are operative to rotate in synchronization with each other.

9. The system of claim 7, further comprising one or more X-ray collimators supported by the working surface of the housing.

10. The system of claim 9, wherein the one or more X-ray collimators are positioned between the plurality of target supports and the plurality of X-ray detector arrays.

* * * * *